United States Patent

Fieggen et al.

[11] Patent Number: 5,565,976
[45] Date of Patent: Oct. 15, 1996

[54] METHOD AND APPARATUS FOR DETECTING AND COMPENSATING FOR A KINK IN AN OPTIC FIBER

[75] Inventors: Bruce Fieggen, Snohomish; Dana Lewis, Woodinville; Linda Sawyer, Seattle, all of Wash.

[73] Assignee: Abbott Laboratories, Abbott Park, Ill.

[21] Appl. No.: 374,104

[22] Filed: Jan. 18, 1995

[51] Int. Cl.$^6$ .......................... G01N 33/48; G08B 21/00; A61B 5/00
[52] U.S. Cl. ...................... 356/39; 128/634; 250/227.16; 250/227.23; 356/41; 356/412
[58] Field of Search ........................ 250/227.16, 227.23, 250/356; 128/634; 356/412, 39, 41

[56] References Cited

U.S. PATENT DOCUMENTS

| | | | |
|---|---|---|---|
| 4,703,175 | 10/1987 | Salour et al. | |
| 4,709,145 | 11/1987 | Spillman, Jr. | |
| 4,727,254 | 2/1988 | Wlodarczyk | 250/338 |
| 5,021,647 | 6/1991 | Tatsuno et al. | 250/227.21 |
| 5,047,627 | 9/1991 | Yim et al. | 250/227.23 |
| 5,177,354 | 1/1993 | Tomita et al. | 250/227.15 |
| 5,262,639 | 11/1993 | Vokey et al. | 250/227.15 |
| 5,300,769 | 4/1994 | Dahlin et al. | 250/227.23 |

Primary Examiner—Vincent P. McGraw
Attorney, Agent, or Firm—Christensen, O'Connor, Johnson & Kindness PLLC

[57] ABSTRACT

A method and apparatus are provided for detecting and compensating for a kink in an optical fiber. A distal sensor (11) monitors a level of a parameter in an environment in which the distal sensor is immersed. The distal sensor is disposed at a tip of the optical fiber (17) and the optical fiber conveys green light signals and near infrared (NIR) light signals to and from the distal sensor. A photodetector (59') records the signal and reference values for the green light signals and the NIR light signals conveyed by the optical fiber at consecutive data points. A microcontroller (42) is electronically coupled to the photodetector and receives the signal and reference values for the green light signals and the NIR light signals. A kink in the optical fiber is detected when a change between NIR signal values recorded at a pair of consecutive data points recorded by the photodetector is greater than a predetermined threshold. After the kink is detected, a true level of the parameter in the environment is calculated that compensates for the kink. More specifically, a true green signal value is determined based on a linear relationship between green and NIR signal values recorded at the pair of consecutive data points. The true green signal value is then used to calculate the true level of the parameter. In an alternative embodiment of the present invention, a warning is issued when the kink is detected and monitoring of the level of the parameter is discontinued.

42 Claims, 10 Drawing Sheets

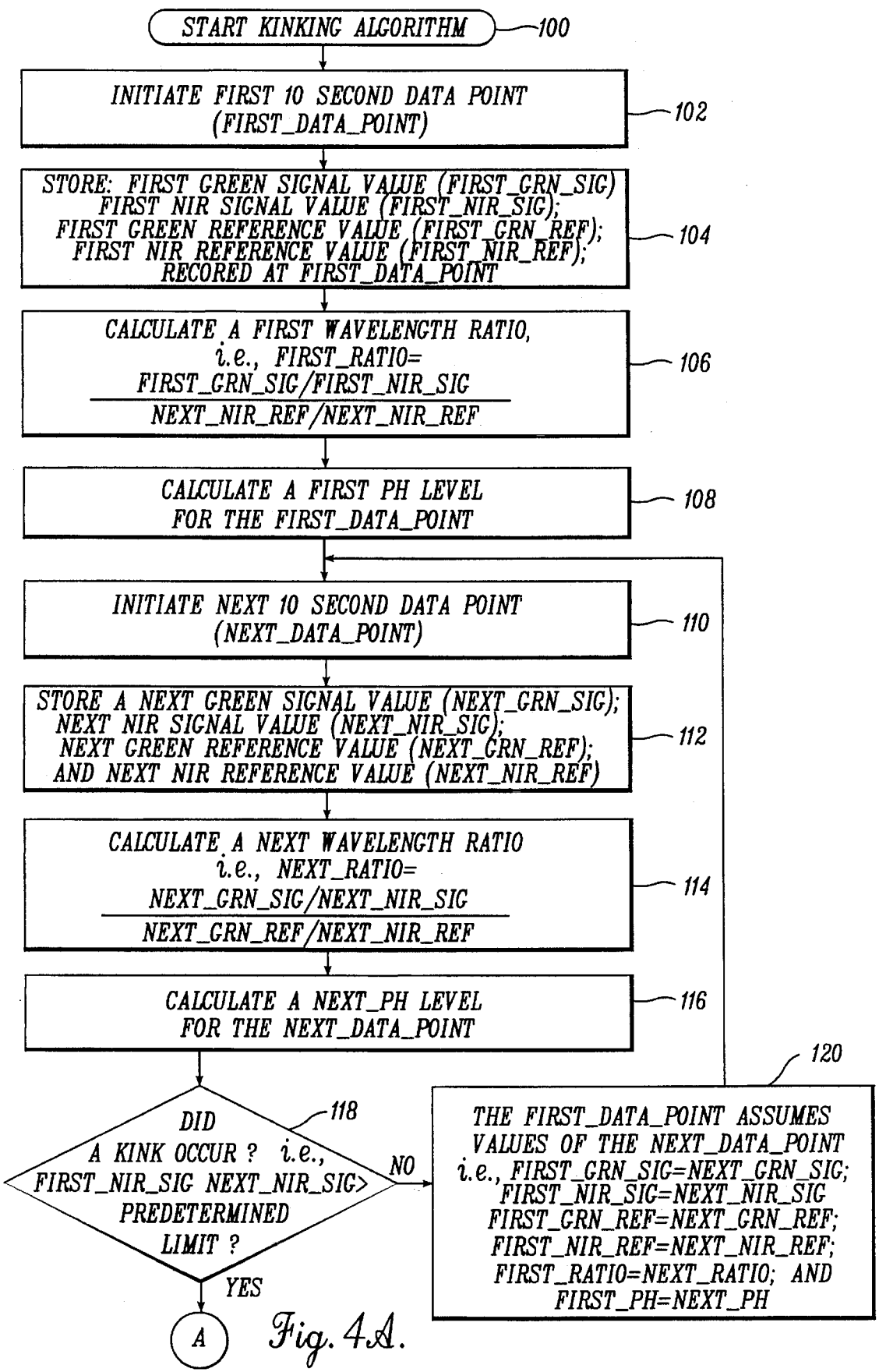

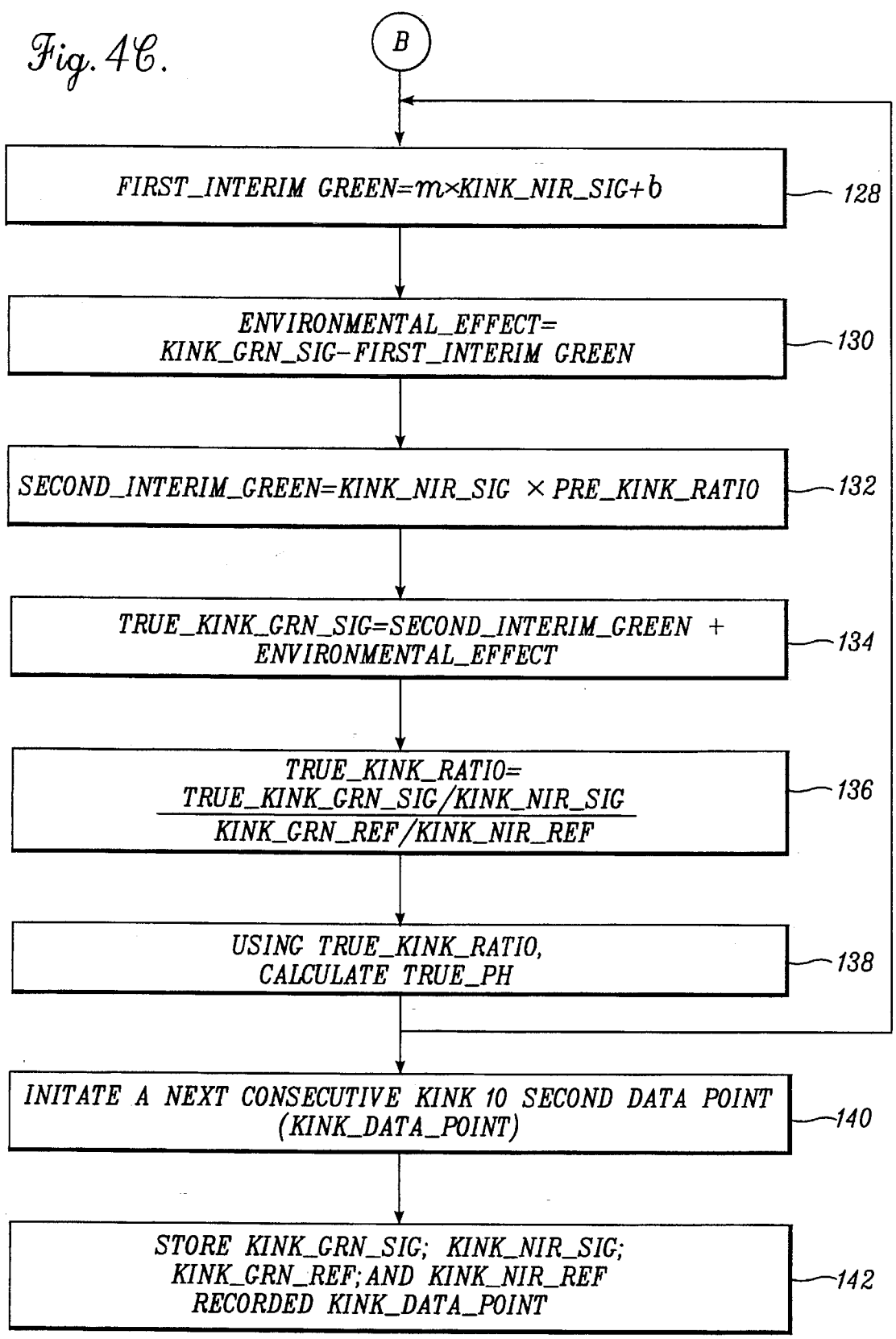

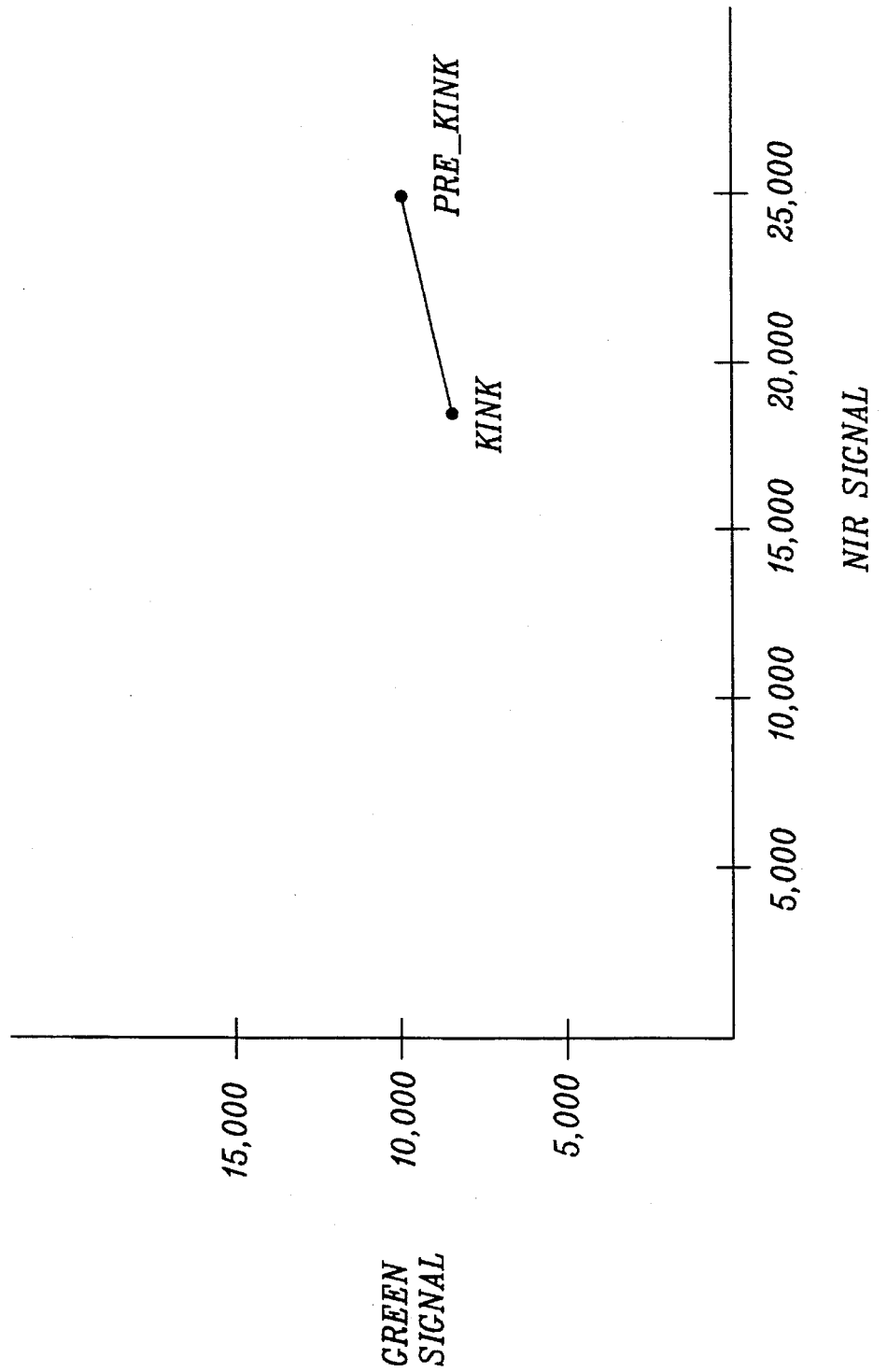

METHOD AND APPARATUS FOR DETECTING AND COMPENSATING FOR A KINK IN AN OPTIC FIBER

FIELD OF THE INVENTION

This invention generally relates to a method and apparatus for detecting and compensating for a kink in an optical fiber having a distal sensor for monitoring parameters, and more specifically, for recalculating the parameters monitored by the distal sensor and/or issuing a warning when a kink in the optical fiber has been detected.

BACKGROUND OF THE INVENTION

Fiber-optic sensors and sensing systems are frequently used to detect the presence and monitor the concentration of various analytes, including oxygen, carbon dioxide, and hydrogen ions (i.e., pH), in both liquid and in gas environments. Such sensors are based on the recognized phenomenon that the absorbence and, in some cases, the luminescence, phosphorescence, or fluorescence of certain indicator molecules are perturbed by the presence of specific analyte molecules in the environment. The perturbation of the light emission properties and/or absorbence profile of an indicator molecule can be detected by monitoring radiation that is absorbed, reflected, or emitted by it when illuminated in the presence of a specific analyte.

Fiber-optic sensors that position an analyte sensitive indicator molecule in a light path optically monitor the effect of the analyte on the indicator molecule. Typically, for monitoring carbon dioxide, pH level, or some other parameter in a particular environment, an optical fiber transmits electromagnetic radiation from a light source to the indicator molecule, and the level of absorbence as measured by the light reflected from the vicinity of the indicator molecule gives an indication of the gaseous or ionic concentration of the analyte. These indicator molecules are typically disposed in a sealed chamber at the distal end of the optical fiber, and the chamber walls are permeable to the analyte of interest.

Fiber-optic sensors are commonly used to monitor the blood gas parameter of a patient where the sensor is located at the end of a catheter that is inserted into the patient. One problem with such sensors is that the optical fibers attached to the end of the sensor are prone to kinking. The optical fibers are delicate because they are situated as an external appendage located at the end of the catheter used to invasively insert the sensor and extend distally beyond it. Any mishandling of the catheter or movement of the patient can easily result in kinking of the optical fibers.

In view of the importance of accurately measuring parameters such as carbon dioxide, oxygen, and pH, there is an existing need to provide a method and apparatus that provides accurate and timely measurements of the parameters being monitored regardless of a kink in the optical fibers. At the very least, the method and apparatus should notify the operator when a kink occurs. The present invention provides a simple and elegant method for detecting and compensating for a kink in an optical fiber that provides accurate and timely measurements, and in the alternative, issues a warning when a kink occurs.

SUMMARY OF THE INVENTION

In accordance with the present invention, a method and apparatus are provided for detecting and compensating for a kink in an optical fiber wherein the optical fiber conveys light signals of a first wavelength and light signals of a second wavelength. A distal sensor monitors a level of a parameter in an environment in which the distal sensor is immersed. The distal sensor is disposed at a tip of the optical fiber and the optical fiber conveys light signals of the first wavelength and light signals of the second wavelength to and from the distal sensor. A photodetector records the reference values for the light signals of the first wavelength and the reference values for the light signals of the second wavelength conveyed to the distal sensor by the optical fiber at consecutive data points. In addition, the photodetector records the signal values for the light signals of the first wavelength and the signal values for the light signals of the second wavelength conveyed from the distal sensor. A processing unit electronically coupled to the photodetector receives the signal and reference values for the light signals of the first wavelength and the signal values for the light signals of the second wavelength. The processing unit also includes memory means for storing program instructions, which control the processing unit causing it to detect a kink in the optical fiber and compensate for the kink when measuring the level of the parameter in the environment. Specifically, the processing unit responds to the programmed instructions to function as storing means, detecting means and measuring means.

The storing means store the signal and reference values for the light signals of the first wavelength and the signal and reference values for the light signals of the second wavelength recorded by the photodetector at consecutive data points. The detecting means then determines if a change between the signal values for light signals of the second wavelength recorded at a pair of consecutive data points is greater than a predetermined threshold. Finally, the measuring means measures an accurate level of the parameter in the environment that compensates for the kink. The measuring means compensates for the kink at consecutive data points when the kink is detected by determining an accurate signal value for light signals of the first wavelength, and measuring the accurate level of the parameter in the environment as a function of the accurate signal value for the light signals of the first wavelength, the signal value for the light signals of the second wavelength, the reference value for the light signals of the first wavelength and the reference value for the light signals of the second wavelength.

More specifically, the measuring means determines the accurate signal value for the light signals of the first wavelength by first, determining a first temporary signal value for the light signals of the first wavelength that linearly corresponds to the change between the signal values for the light signals of the second wavelength recorded at the pair of consecutive data points. Next the measuring means determines an effect of a change in the environment on the signal values of the first wavelength by offsetting the first temporary signal value for the light signals of the first wavelength. Third, the measuring means determines a second temporary signal value for the light signals of the first wavelength that factors out the effect of the kink on the signal values of the first wavelength. Finally, the measuring means combines the second temporary signal value and the effect of the change in the environment.

In a preferred embodiment of the present invention, the distal sensor monitors levels of a plurality of parameters in the environment, wherein the distal sensor is disposed at tips of a plurality of optical fibers and each optical fiber conveys light signals of the first wavelength and light signals of the second wavelength to and from the distal sensor. In addition, a photodetector records the signal and reference values for the light signals of the first wavelength and the signal and values for the light signals of the second wavelength conveyed by each of the optical fibers at consecutive data points. Consequently, the processing unit coupled to the photodetectors detects and compensates for kinks in each of the optical fibers.

A method including steps generally consistent with the functions implemented by the elements of the apparatus described above is a further aspect of this invention.

In an alternative embodiment of the present invention, a method is provided that issues a warning when a kink in the optical fiber is detected as opposed to compensating for the kink. Specifically, if a difference between a current median value for the light signal of the second wavelength and a previous median value for the light signal of the second wavelength is greater than a predefined value threshold, and if a difference between a current median parameter measurement and a previous median parameter measurement is greater than a predefined parameter threshold, a kink is detected and a warning is issued. If a permanent kink is then confirmed, a final warning is issued and the parameter is no longer monitored.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 4A, 4B and 4C are flow charts illustrating the steps used to detect and compensate for a kink in the optical fiber;

FIG. 5 is a graph illustrating a linear relationship between a point at which the optical fiber is kinked and a point at which the optical fiber is not kinked.

DETAILED DESCRIPTION OF THE PREFERRED EMBODIMENT

Figure 2:
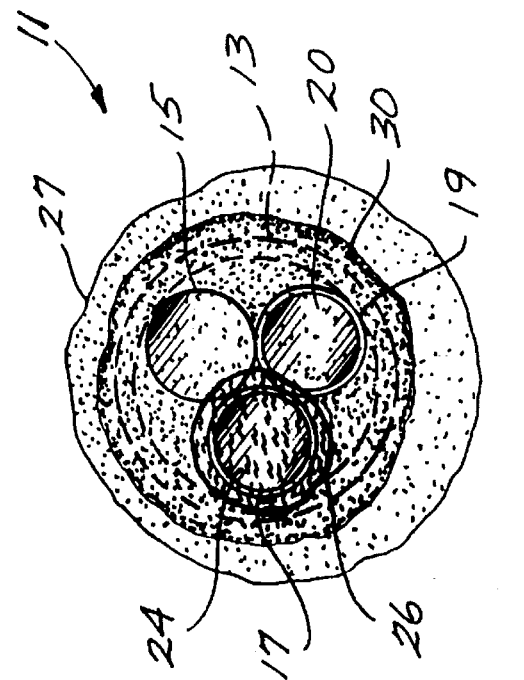
FIG. 2 is an end view of FIG. 1.
Figure 1:
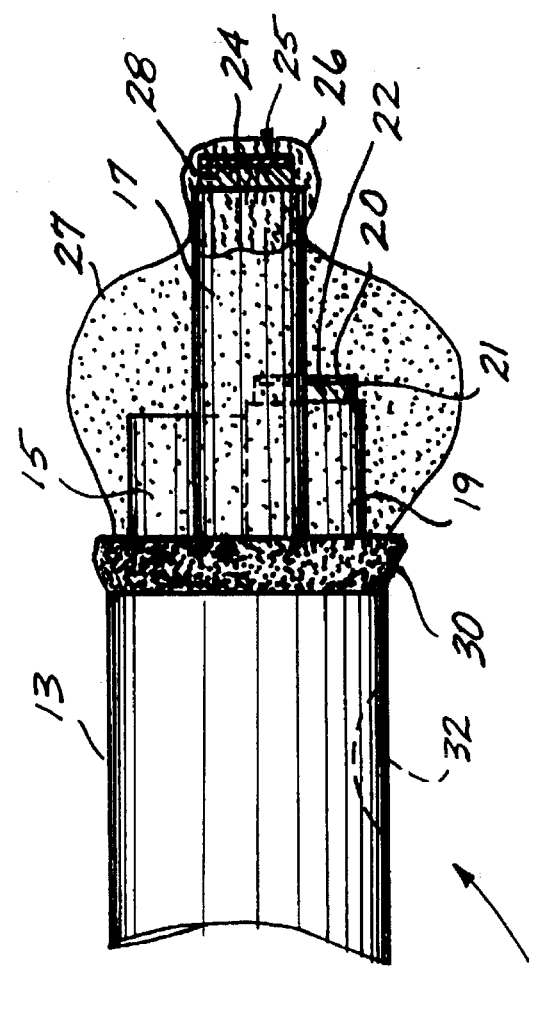
FIG. 1 is a schematic longitudinal view of a conventional fiber-optic probe sensor.

One type of fiber-optic sensor that is useful in the method and apparatus of the present invention is described in commonly assigned U.S. Pat. No. 5,047,627, the disclosure of which is incorporated herein by reference. Referring to FIGS. 1 and in the present application, fiber-optic probe sensor 11 of U.S. Pat. No. 5,047,627 is illustrated and described. The numbering convention for FIGS. 1 and 2 of this application correspond to the numbering convention used in the specification and drawings of the '627 patent. The disclosed fiber-optic sensor is for monitoring chemical parameters but it should be understood that the present invention has equal utility for fiber-optic sensors that monitor non-chemical parameters.

Figure 3:
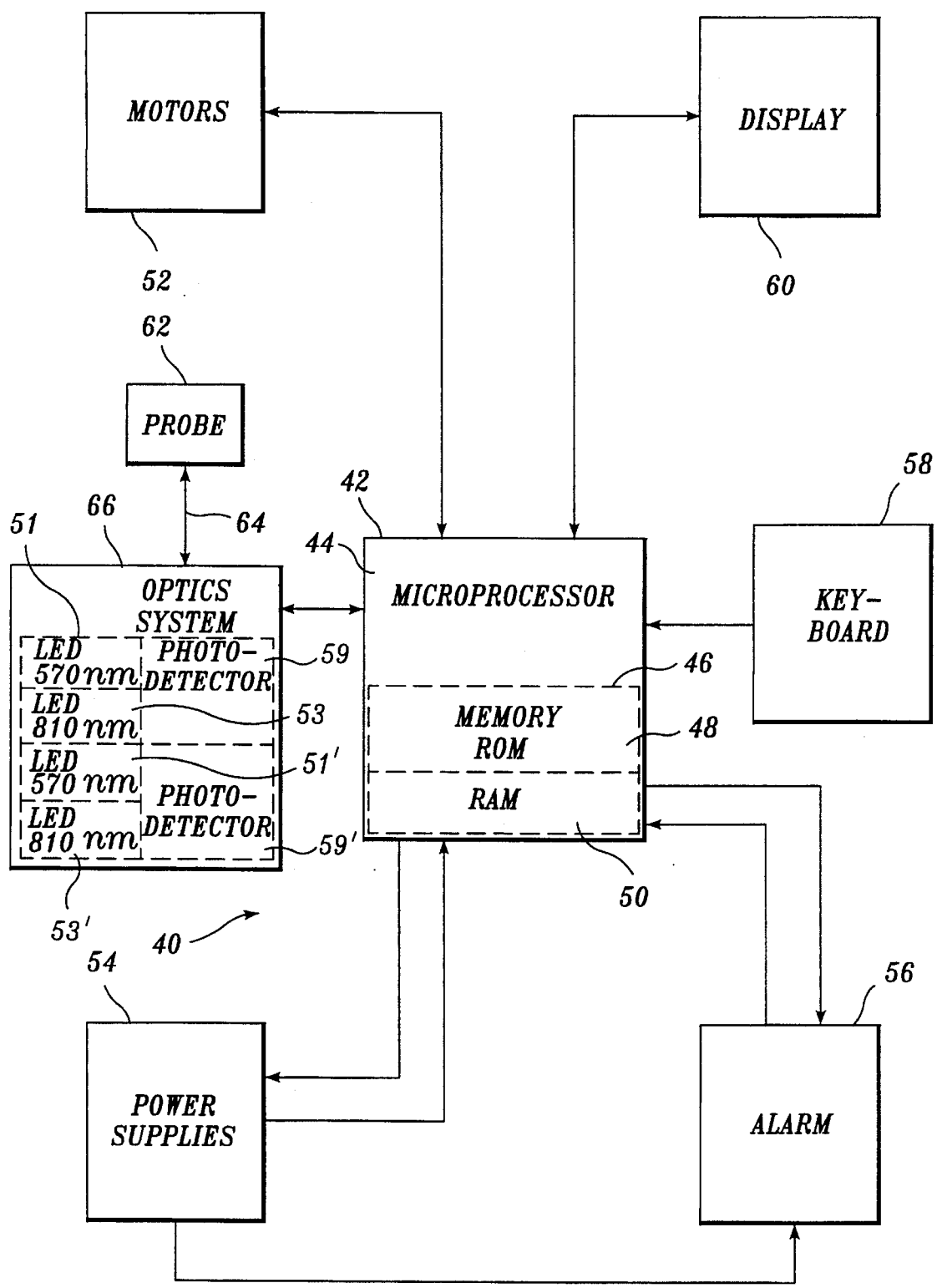
FIG. 3 is an electrical schematic block diagram of a control for a fiber-optic sensing system in which the present invention is used to detect and compensate for a kink in an optical fiber.

Fiber-optic sensor 11 comprises three individual optical fibers 15, 17 and 19, encased in a polyimide sheath 13. (Together, optical fibers 15, 17 and 19, and polyimide sheath 13 form fiber-optic cable 64 as shown in FIG. 3). More specifically, the three optical fibers are arranged such that their longitudinal axes (the axes generally corresponding to the path of a light signal propagating therein) are parallel and arranged in an equilateral triangle array. Optical fiber 15 conveys light signals used to sense oxygen ($O_2$) concentration, optical fiber 17 is used to convey light signals for sensing hydrogen ion (pH) concentration, and optical fiber 19 is used for conveying light signals for sensing carbon dioxide ($CO_2$) concentration. For purposes of this application, however, only $CO_2$ optical fiber 19 and pH optical fiber 17 shall be discussed.

The distal ends of the optical fibers are cleaved perpendicularly to their longitudinal axis, and each distal end comprises a substantial planar, circular surface. Disposed upon the circular surface of $CO_2$ optical fiber 19 is a substantially cylindrical $CO_2$ pellet 21 (i.e., a sensor for $CO_2$ in pellet form) having a diameter approximately equal to that of $CO_2$ optical fiber 19. $CO_2$ pellet 21 includes a $CO_2$ analyte sensitive matrix material 22 and a thin film of reflective material 20. $CO_2$ analyte sensitive matrix material 22 absorbs light signals having certain wavelengths to a degree dependent on the concentration of $CO_2$ in the environment in which the pellet 21 is immersed. The thin film of reflective material 20 is incorporated onto the distal circular surface of $CO_2$ pellet 21, is substantially concentric with a cylindrical surface of the $CO_2$ pellet 21, and is situated such that a light signal propagated through $CO_2$ optical fiber 19 and $CO_2$ pellet 21 is reflected by reflective material 20 back into $CO_2$ optical fiber 19.

Similarly, a cylindrical pH pellet 25 (i.e., a sensor for pH in pellet form) is attached to the distal end of pH optical fiber 17. pH pellet 25 is sized so as to substantially cover the entire circular surface of the distal end of pH optical fiber 17, and includes a pH analyte sensitive material 28 and a thin film of reflective material 24. pH analyte sensitive material 28 absorbs light signals having certain wavelengths to a degree dependent on the concentration of hydrogen ions around pH pellet 25. The thin film of reflective material 24 is incorporated onto the distal circular surface of pH pellet 25, is substantially concentric with the surface of pH pellet 25, and is situated such that a light signal propagated down pH optical fiber 17 and through pH pellet 25 is reflected by reflective material 24 back into pH optical fiber 17.

Referring to FIG. 3, fiber-optic sensor 11 described above and described in more detail in U.S. Pat. No. 5,047,627 can be used in a fiber-optic sensing system 40. The fiber-optic sensing system includes a microcontroller 42 that is programmed to record the parameters of the blood gas environment monitored by the fiber-optic sensor 11. However, it will be appreciated by those of ordinary skill in the art that fiber-optic sensing system 40 may include a more sophisticated microcontroller or even a microcomputer. The microcontroller comprises a microprocessor 44 and a memory 46. This memory includes both a read-only memory (ROM) 48 and a random access memory (RAM) 50. The microprocessor responds to programmed instructions stored in ROM 48 and maintains values temporarily in RAM 50. Also connected to microprocessor 44 are motors 52, a power supply 54, an alarm 56, a keyboard 58 and a display 60. Display 60 selectively produces visual messages that alert the operator of the fiber-optic sensor 11 of a kink in the optical fibers 17 and 19 of fiber-optic cable 64. In addition, display 60 produces visual messages indicating the levels or concentrations of the pH and $CO_2$ parameters being monitored by the fiber-optic sensor. Fiber-optic sensor 11 is integrated into the fiber-optic sensing system 40 via an optic system 66.

Optic system 66 is described in more detail in commonly assigned U.S. Pat. No. 5,300,769, the disclosure of which is incorporated herein by reference. For purposes of this discussion, however, only a few elements of the optic system will be described. The optic system 66 comprises two light-emitting diodes (LED) light sources 51 and 51' that produce light signals having a wavelength in the green region of the visible spectrum of about 570 nanometers and two LED light sources 53 and 53' that produce light signals having a wavelength in the near infrared (NIR) region of the electromagnetic spectrum of about 810 nanometers. LEDs 51 and 53 are used to determine $CO_2$ concentration, while LEDs 51' and 53' are used to determine pH levels.

Light signals having a wavelength in the green region and light signals having a wavelength in the NIR region are transmitted through the fiber optic cable 64 at microsecond intervals. In the case of the $CO_2$ optical fiber 19, the green light signal transmitted by LED 51 is partially absorbed by $CO_2$ analyte sensitive matrix 22 and $CO_2$ pellet 21 to a degree that depends on the concentration of the $CO_2$ in the blood gas environment around $CO_2$ pellet 21. The attenuated green light signal is reflected by reflective material 20 and propagated back as the return reflected green light signal into $CO_2$ optical fiber 19. The absorption of NIR light signals from LED 53 is negligible and not affected by $CO_2$ concentration. Accordingly, the NIR light signal from LED 53 is transmitted through the $CO_2$ analyte sensitive matrix 22 and $CO_2$ pellet 21 and is reflected back, relatively unattenuated, into $CO_2$ optical fiber 19. A photodetector 59 records the amplitude of both the green and NIR light signals sent (reference values) and the amplitude of the green and NIR return reflected signals (signal values). The green and NIR signal values recorded by photodetector 59 are transmitted to the microcontroller 42, which uses the values to calculate the concentration of $CO_2$ in the blood gas environment surrounding $CO_2$ pellet 21.

The operation of the pH sensing portion of the fiber-optic sensing system 40 is similar to the above-described $CO_2$ sensing portion. The green light signal emitted from LED 51' is transmitted to the distal end of pH optical fiber 17, where the green light signal is partially absorbed by pH pellet 25 as a function of hydrogen ion concentration in the blood gas environment around pH pellet 25. The attenuated green light signal is reflected back into pH optical fiber 17 by the layer of reflective material 24 in pH pellet 25. The absorption of light signals from LED 53' in pH pellet 25 is negligible and is not affected by hydrogen ion concentration (pH) of the blood gas environment around the pellet 25. Accordingly, the NIX light signal remains relatively unattenuated and is reflected back into pH optical fiber 17. A photodetector 59' in the optic system 66 records the amplitudes of both the green and NIR light signals sent (reference values) and the amplitudes of the green and NIR returned reflected light signals (signal values). The green and NIR signal values recorded by the photodetector 59' are transmitted to the microcontroller 42, which uses the values to calculate the concentration of hydrogen ions (i.e., the pH level) in the blood gas environment around pH pellet 25.

A kink in the fiber-optic cable 64 may occur at any time during the life of the fiber-optic sensor 11. A kink usually tends to affect one optical fiber within the fiber-optic cable more than another. More specifically, kinks may occur which cause a physical kink in the polyimide sheath 13 of the fiber-optic cable. The optical fiber lying next to the inside curve of the polyimide sheath may be more affected by the kink. As a result, the return reflected NIR light signal being transmitted through that optical fiber becomes attenuated, causing an incorrect calculation of the pH level or $CO_2$ concentration being monitored by the fiber-optic sensor. The algorithms of the present invention detect such kinks and respond accordingly. In a first preferred embodiment of the present invention, a kinking algorithm detects the kink in the affected optical fiber and compensates for the kink when measuring the level of the parameter. In another preferred embodiment of the present invention, a warning algorithm detects the kink and issues a warning to the operator.

Figure 4B:
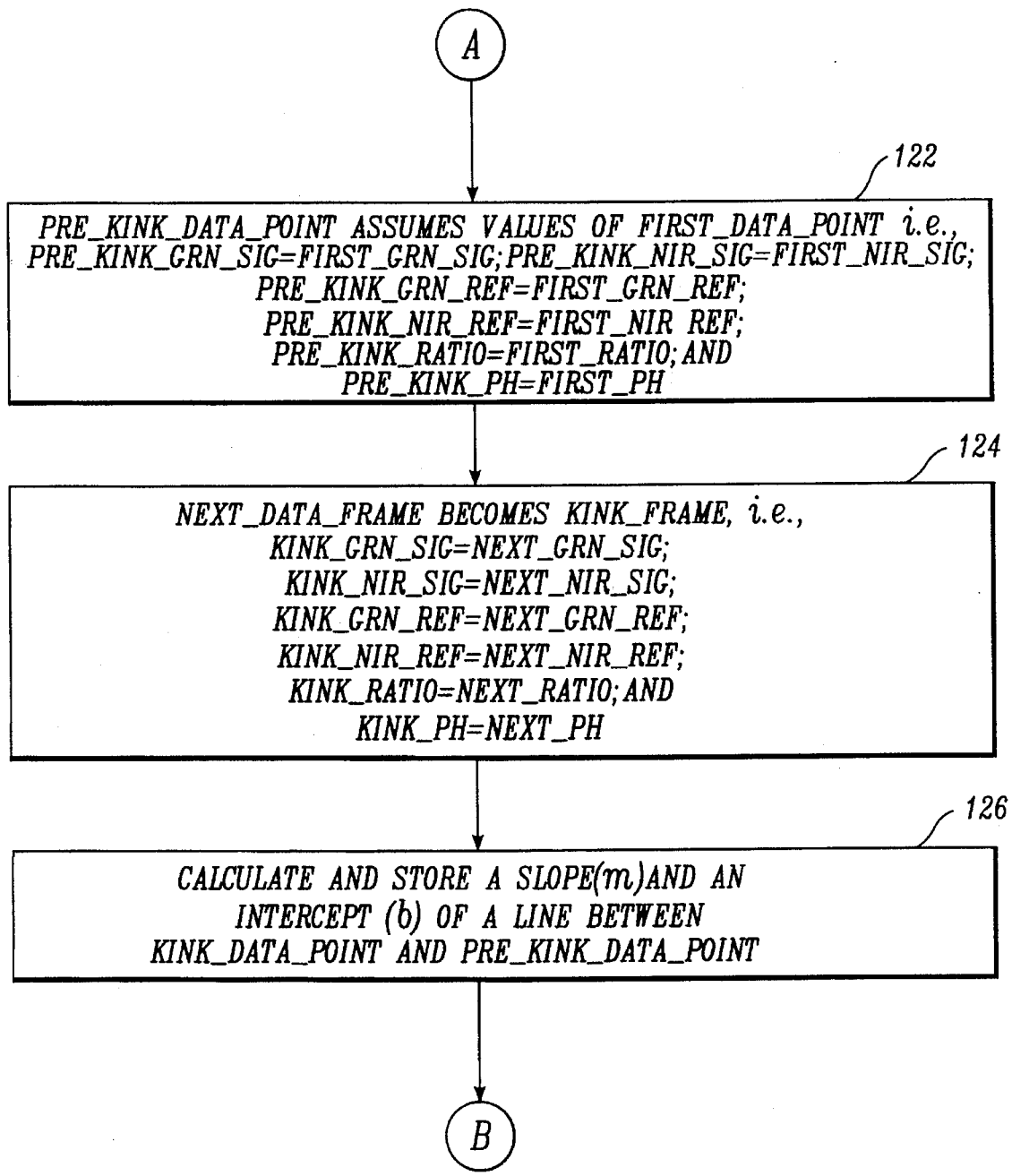

The logic implemented in the first preferred embodiment of the present invention is illustrated in FIGS. 4A through 4C where a kink in the pH optical fiber 17 is detected. It will be appreciated by those of ordinary skill in the art that the first preferred embodiment of the present invention as described may be used simultaneously to detect and compensate for a kink in $CO_2$ optical fiber 19. In addition, it should be recognized that the kinking algorithm may be used to detect and compensate for kinks in optical fibers used to monitor both chemical and non-chemical parameters.

The kinking algorithm begins immediately upon insertion of the fiber-optic sensor 11 into a patient's blood stream and continues for the life of the fiber-optic sensor. Hence, the logic begins in a block 100 of FIG. 4A as the fiber-optic sensor begins monitoring the pH level in the blood gas environment and as green and NIR light signals are first emitted from LEDs 51' and 53' and transmitted to the distal end of pH optical fiber 17. In a block 102, a first 10-second data point is initiated. At this and all successive 10-second data points, the photodetector 59' records a green signal value and a NIR signal value for the green and NIR light signals reflected back into pH optical fiber 17 by the pH pellet 25. In addition, photodetector 59' records a green reference value and a NIR reference value for the green and NIR light signals sent to the pH pellet 25 through optical fiber 17. Hence, in a block 104 a first green signal value, a first NIR signal value, a first green reference value and a first NIR reference value recorded by the photodetector 59' at the first 10-second data point, are stored in RAM 50 of the microcontroller 42. Within microseconds of storing these values, the microcontroller determines a first wavelength ratio of first green and NIR light signal amplitudes. More specifically, the first ratio is obtained in a block 106 by dividing a ratio of first green signal value to first NIR signal value by a ratio of first green reference value to first NIR reference value. In a block 108, the microcontroller calculates s first pH level in the blood gas environment monitored by the fiber-optic sensor at the first data point as a function of the first ratio, i.e., by comparing the ratio of first green signal value to first NIR signal value to the ratio of first green reference value to first NIR reference value as described in commonly assigned U.S. Pat. Nos. 5,300,769 and 5,047,627.

In a block 110, a next 10-second data point is initiated. At the next data point, a next green signal value, a next NIR signal value, a next green reference value and a next NIR reference value are stored in a block 112. Proceeding to a block 114, a next wavelength ratio is calculated by dividing a ratio of next green signal value to next NIR signal value by a ratio of next green reference value to next NIR reference value. In a block 116, a next pH level monitored by the fiber-optic sensor 11 at the next data point is calculated as a function of the next ratio, i.e., by comparing the ratio of next green signal value to next NIR signal value to the ratio of next green reference value to next NIR reference value. It is important to note that the next ratio will approximate the first ratio as long as the pH level in the blood gas environment remains constant, i.e., the wavelength ratio remains constant as long as the pH level remains constant.

Proceeding to a decision block 118, the logic determines if a kink has occurred by comparing the first and next NIR signal values stored at the first and next data points. More specifically, the logic determines if a difference between the first NIR signal value and the next NIR signal value is greater than a predetermined limit. Since the absorption of NIR light signals is not affected by the hydrogen ion concentration in the blood gas environment, NIR signal values remain relatively constant when the pH level of the environment changes. Consequently, any significant difference between the first and next NIR signal values (i.e., a change in NIR signal values greater than the predetermined limit) is most likely the result of a kink in the optical fiber 17. In the preferred embodiment, the predetermined limit is selected based on empirical data, which has demonstrated that a change in NIR signal value of more than 500 counts indicates a kink.

If the difference between the first and next NIR signal values is not greater than the empirically selected predetermined limit, a kink has not occurred. Hence, the microcontroller 42 continues recording and comparing first and next NIR signal values. In this regard, the logic proceeds to a block 120 where the first data point assumes the values associated with the next data point. More specifically, the microcontroller sets the first green signal value equal to the next green signal value, the first NIR signal value equal to the next NIR value, the first green reference value equal to the next green reference value, the first NIR reference value equal to the next NIR reference value, the first ratio equal to the next ratio, and the first pH level equal to the next pH level. The logic then returns to blocks 110 through 116 where a next consecutive 10-second data point is initiated; a next green and a next NIR signal value, and a next green and a next NIR signal value are stored, a next ratio is calculated; and a next pH level is determined. In decision block 118, the logic once again tests for a kink by comparing the first and next NIR signal values stored at the first and next data points. The comparison between first and next NIR signal values continues in the manner described above until a kink occurs, causing the logic to proceed from block 118 to a block 122 as shown in FIG. 4B.

When the kink is detected, the first and next data points are identified by the microcontroller 42 as a pre-kink data point and a kink data point, respectively, for the remaining life of the fiber-optic sensor 11. More specifically, in block 122 the pre-kink data point assumes the values associated with the first data point, and the microcontroller stores a pre-kink green signal value equal to the first green signal value, a pre-kink NIR signal value equal to the first NIR signal value, a pre-kink green reference value equal to the first green reference value, a pre-kink NIR reference value equal to the first NIR reference value, a pre-kink ratio equal to the first ratio, and a pre-kink pH level equal to the first pH level. The logic then proceeds to a block 124 where the kink data point assumes the values associated with the next data point; and microcontroller stores a kink green signal value equal to the next green signal value, a kink green reference value equal to the next green reference value, a kink NIR reference value equal to the next NIR reference value, a kink NIR signal value equal to the next NIR signal value, a kink ratio equal to the next ratio, and a kink pH level equal to the next pH level.

Once the kink has been detected and the values assumed by the pre-kink data point and kink data point have been stored, the microcontroller 42 uses the pre-kink and kink green and NIR signal values to compensate for the kink in calculating the pH level for the remaining life of the fiber-optic sensor 11. In this regard, applicants have discovered that a linear relationship exists between the kink green and NIR signal values at the kink data point and the pre-kink green and NIR signal values at the pre-kink data point. Hence, as shown in FIG. 5, a straight line may be drawn from the kink data point defined by the kink green signal value and kink NIR signal value, to the pre-kink data point defined by the pre-kink green signal value and pre-kink NIR signal value, where a y-axis represents green signal values and an x-axis represents NIR signal values. Hence, a kink equation representing such a line and the linear relationship between the kink data point and pre-kink data point may be defined as:

$$\text{Green Signal Value} = m \times \text{NIR Signal Value} + b,$$

where m is a slope of the line and b is an intercept of the line.

The kink equation represents the effect of kinking on the NIR light signals and green light signals associated with a particular fiber-optic sensor at a particular time. In other words, the green signal value linearly corresponds to a change in NIR signal value caused by a kink. However, the kink equation does not account for any change in the pH level in the blood gas environment. In a block 126, the slope (m) and the intercept (b) of the line between the kink and pre-kink data points are calculated and stored by the microcontroller using the above kink equation applied to the pre-kink and kink green and NIR signal values and well known algebraic methods. The slope (m) and intercept (b) is then used to determine a true pH level that compensates for the kink for the remaining life of the fiber-optic sensor 11.

Since the kink in optical fiber 17 has corrupted the kink green and NIR signal values, the kink has also corrupted the kink ratio and the kink pH level originally calculated at the kink data point. In order to calculate the true pH level at the kink data point, the microcontroller 42 must first compensate for the kink and recalculate the kink ratio. More specifically, the microcontroller must calculate a true kink green signal value that both compensates for the kink and reflects any change in the pH level in the blood gas environment. Then using the true kink green signal value, the microcontroller may calculate a true kink ratio and in turn, the true pH level.

As shown in FIG. 4C, the true kink green signal value is calculated by the microcontroller 42 in four stages using the slope (m), intercept (b), and pre-kink green and NIR signal values ratio calculated and stored above. First, the kink equation is applied to the kink NIR signal value to determine a first interim green signal value that represents what the kink green signal value should have been due to the amount of kinking shown by the kink NIR signal value. In making this determination, the microcontroller assumes that the pH level in the blood gas environment has remained constant, i.e., that the attenuation of the green and NIR light signals represented by the kink green and NIR signal values is due solely to the kink. Hence, in a block 128 the microcontroller applies the kink equation to the kink NIR signal value to determine the first interim green signal value as follows:

$$\text{First Interim Green Signal Value} = m \times \text{Kink NIR Signal Value} + b.$$

However, the first interim green signal value still may not represent the true green signal value. The microcontroller 42 must still account for the effect, if any, of a change in the pH level in the blood gas environment surrounding the fiber-optic sensor 11. As noted earlier, it is the green signal value, and not the NIR signal value, that is affected by a change in pH level in the blood gas environment. Therefore, the effect of the change in pH level (or environmental effect) is determined by calculating a difference between the kink green signal value and the first interim green signal value. Hence, the second stage in calculating the true green signal value is carried out by the microcontroller in a block 130 using the following equation:

Environmental Effect=Kink Green Signal Value−First Interim Green Signal Value.

The environmental effect determined using the first interim green signal value is ultimately used to calculate the true kink green signal value. However, before the true green signal can be calculated using the environmental effect, the microcontroller 42 must calculate a second interim green signal value that represents what the kink green signal value should have been, had proper compensation been made for the kink. As noted earlier, if the pH level in the blood gas environment remains constant, the wavelength ratio of green and NIR light signal amplitudes should remain constant as well. However, in the presence of a kink, the kink ratio tends toward the value 1 because the kink has corrupted the kink green and NIR signal values used to calculate the kink ratio. In order to compensate for the kink, applicants have discovered that if the kink NIR signal value is multiplied by a pre-kink signal ratio of pre-kink green signal value to pre-kink NIR signal value, the pre-kink signal ratio may factor out the corruptive effect of the kink on the kink green signal value. Hence, in a block 132, the microcontroller carries out the third stage in calculating the true green signal value and calculates the second interim green signal value using the following equation:

Second Interim Green Signal Value=Kink NIR Signal Value×(Pre-Kink Green Signal Value÷Pre-Kink NIR Signal Value), wherein the pre-kink green signal value divided by the pre-kink NIR signal value is equal to the pre-kink signal ratio.

Finally, the true kink green signal value that both compensates for the kink in optical fiber 17 and reflects any change in the pH level in the blood gas environment monitored by fiber-optic sensor 11 is calculated in a fourth stage. In a block 134, the microcontroller 42 adds the second interim green signal value and the environmental effect to obtain the true kink green signal value. In a block 136, a true kink ratio is obtained by dividing the ratio of true kink green signal value to kink NIR signal value by the ratio of kink green reference value to kink NIR reference value; and in a block 138, the true pH level is calculated as a function of the true kink ratio.

Since the kink continues to affect the fiber-optic sensor 11 indefinitely, compensation for the kink must continue indefinitely. Consequently, the logic proceeds to a block 140 where a subsequent consecutive 10-second data point in the life of the fiber-optic sensor 11 begins. However, since the kink has already been detected, the subsequent consecutive 10-second data point is also referred to as a kink data point. In a block 142, a kink green signal value, a kink NIR signal value, a kink green reference value and a kink NIR reference value recorded by the photodetector 59' are stored in RAM 50 of microcontroller 42. The logic then returns to block 128 and repeats blocks 128 through 142 for the remaining life of the fiber-optic sensor, thus ensuring that the true pH level is calculated for all subsequent kink data points. It will be appreciated that any recalculation of the slope(m), intercept(b), and the pre-kink signal ratio is unnecessary because the linear relationship between the kink point and the pre-kink point of the optical fiber 17 applies to all kink green and NIR signal values for the remaining life of the fiber-optic sensor. It should be appreciated that this linear relationship compensates for any subsequent kinks in the optical fiber. In addition, this linear relationship applies to light signals of wavelengths other than those in the green region of the visible spectrum and in the NIR region of the electromagnetic spectrum provided that one of the light signals is affected by the concentration of a parameter in an environment and the other light signal is not.

As opposed to the kinking algorithm described above for detecting and compensating for a kink in an optical fiber or in conjunction with the kinking algorithm, it may be desirable for the microcontroller 42 to employ a warning algorithm for issuing a warning to the operator when the kink occurs. In this regard, FIGS. 6A through 6D are flow charts illustrating the logic implemented in a preferred embodiment of the warning algorithm used to detect a kink in the pH optical fiber 17 and issue a warning. It will be appreciated that in the preferred embodiment, the warning algorithm is applied simultaneously to the $CO_2$ and pH parameters to detect kinks in $CO_2$ optical fiber 19 and pH optical-fiber 17. In addition, one of ordinary skill in the art will recognize that the warning algorithm may be used to detect kinks in optical fibers used to monitor both chemical and non-chemical parameters.

As in the kinking algorithm, the warning algorithm begins immediately upon insertion of the fiber-optic sensor 11 into the patient's blood stream. Hence, the logic begins in a block 150 in FIG. 6A as the fiber-optic sensor begins monitoring the pH level in the blood gas environment and as the green and NIR light signals are first emitted from LEDs 51' and 53' and transmitted to the distal end of pH optical fiber 17. However, as opposed to storing and comparing first and next consecutive 10-second data points to detect a kink in the optical fiber as in the kinking algorithm, in the warning algorithm the microcontroller 42 stores and compares 10-second data points that are 120 seconds apart. More specifically, in the warning algorithm, a current 30-second window comprising values associated with three most recently stored data points is compared to a previous 30-second window comprising values associated with three data points stored 120 seconds earlier. The logic implemented by the microcontroller to compare the current and previous 30-second windows will now be discussed in further detail.

After the warning algorithm begins in block 150, the logic proceeds to a block 152 where a data point counter n that keeps track of the number of data points is initialized to 0. In blocks 154 and 156, the data point counter n is incremented and a 10-second data point ($DP_n$) is initiated by the microcontroller 42. In a block 158, a green reference value ($GR_n$), a NIR reference value ($NR_n$), a green signal value ($GS_n$) and a NIR signal value ($NS_n$) that are recorded by photodetector 59' at data point $DP_n$ are stored in RAM 50 of microcontroller 42. Within microseconds of storing these values, the microcontroller determines a wavelength ratio ($\lambda_n$) by dividing a ratio of green signal value to NIR signal value ($GS_n/NS_n$) by a ratio of green reference value to NIR reference value ($GR_n/NR_n$). More specifically, in a block 160 the microcontroller calculates the wavelength ratio $\lambda_n$ using the following formula:

$$\lambda_n = (GS_n/NS_n) \div (GR_n/NR_n).$$

Finally, in a block 162, the microcontroller calculates a pH level ($pH_n$) in the blood gas environment being monitored by the fiber-optic sensor 11 at the data point $DP_n$ as a function of the wavelength ratio $\lambda_n$, i.e., by comparing the ratio of green signal value to NIR signal value to the ratio of green reference value to NIR reference value as described in commonly assigned U.S. Pat. Nos. 5,300,769 and 5,098,659.

The logic then proceeds to a decision block 164, where it determines if the data point counter n equals four. In other words, the logic determines if enough time has passed so that the values comprising the previous 30-second window can be initialized. If the results are negative, the logic returns to block 154 and the data point counter n is incremented. Consequently, blocks 154 through 162 are repeated until the data point counter n equals four and consecutive green reference values ($GR_4$, $GR_3$, $GR_2$ and $GR_1$), NIR reference values ($NR_4$, $NR_3$, $NR_2$ and $NR_1$), green signal values ($GS_4$, $GS_3$, $GS_2$ and $GS_1$), NIR signal values ($NS_4$, $NS_3$, $NS_2$ and $NS_1$), wavelength ratios ($\lambda_4$, $\lambda_3$, $\lambda_2$ and $\lambda_1$) and pH levels ($pH_4$, $pH_3$, $pH_2$ and $pH_1$) have been stored at four consecutive data points ($DP_4$, $DP_3$, $DP_2$ and $DP_1$). When this occurs, the logic proceeds to blocks 166 through 170 where the values comprising the previous window are initialized. In block 166, where a previous data point counter m is set equal to the data point counter n minus 1 so that the counter m identifies the data point ($DP_m$) at which the previous window is initialized. In a block 168 a previous median NIR signal value is determined by the microcontroller by taking the median of the three consecutive NIR signal values $NS_m$, $NS_{m-1}$ and $NS_{m-2}$ stored at the three consecutive data points $DP_m$, $DP_{m-1}$ and $DP_{m-2}$, i.e., by taking the median of the first three consecutive NIR signal values $NS_3$, $NS_2$ and $NS_1$ at the first three consecutive data points $DP_3$, $DP_{m2}$ and $DP_1$. Now referring to a block 170 in FIG. 6B, a previous median pH level associated with the previous window is calculated by taking the median of the three consecutive pH levels $pH_m$, $pH_{m-1}$ and $pH_{m-2}$ calculated at the three consecutive data points $DP_m$, $DP_{m-1}$ and $DP_{m-2}$, i.e., by taking the median of the first three consecutive pH levels $pH_3$, $pH_2$ and $pH_1$ at the first three consecutive data points $DP_3$, $DP_2$ and $DP_1$.

Now that the previous window has been initialized, the microcontroller must initialize the current 30-second window, 120 seconds later. To initialize the values comprising the current 30-second window, the microcontroller 42 continues to store and calculate the green and NIR reference and signal values, the wavelength ratio and the pH level for twelve more consecutive 10-second data points, i.e., for 120 seconds. Accordingly, the data point counter n is incremented in a block 172. One will note, however, that the previous data point counter m is not incremented. Previous data point counter m is only incremented after this 120 second period is over and the values comprising the current window are initialized. In a block 174, green reference value $GR_n$, NIR reference value $NR_n$, green signal value $GS_n$ and NIR signal value $NS_n$ recorded at consecutive data point $DP_n$ are stored. In a block 176, wavelength ratio $\lambda_n$ and pH level $pH_n$ are calculated as previously described. The logic then proceeds to a decision block 178, where the logic determines if the data point counter n is equal to the previous data point counter m plus 12. In other words, the logic determines if 120 seconds have passed since the values comprising the previous window have been calculated. If the results are negative the logic returns to block 170 and repeats blocks 170 through 176 until the values enumerated above have been stored and calculated for twelve consecutive data points, i.e., until 120 seconds have passed.

If the results of decision block 178 are positive, the logic proceeds to blocks 180 and 182 so that the current window may be initialized using values stored at data points 120 seconds after the previous window was initialized. In block 180, the microcontroller 42 determines a current median NIR value by taking the median of three most recently stored NIR signal values $NS_n$, $NS_{n-1}$ and $NS_{n-2}$ stored over three most recent data points $DP_n$, $DP_{n-1}$ and $DP_{n-2}$. In block 182, the microcontroller determines a current median pH level by taking the median value of the three most recently stored pH levels $pH_n$, $pH_{n-1}$ and $pH_{n-2}$ calculated over the three most recent data points $DP_n$, $DP_{n-1}$ and $DP_{n-2}$.

Once the values comprising the current and previous windows have been initialized, they are compared to determine if a possible kink has occurred in optical fiber 17. The logic proceeds to a decision block 184, where the logic compares the current median values associated with the current window to the old median values associated with the previous window, looking for a significant change in NIR signal value and an accompanying significant change in pH level. More specifically, the logic in decision block 184 determines if an absolute value of a difference between the current median NIR signal value and the previous median NIR signal value is greater than a predetermined NIR limit; and if an absolute value of a difference between the current median pH level and the previous median pH level is greater than a predetermined pH level limit. In the preferred embodiment of the warning algorithm, the predetermined NIR limit and the predetermined pH level limit are selected based upon empirical data. However, the predetermined NIR and pH level limits may be modified as desired to detect either very large or very small NIR signal changes. For example, if the warning algorithm does not detect kinks as required, the warning algorithm may be disabled by increasing the predetermined NIR and pH limits.

If the decision in block 184 is negative, a kink has not occurred and testing for a kink must continue. Consequently, the values comprising both the previous window and the current window must be updated. In this regard, the logic proceeds to a block 186, where the previous data point counter m is finally incremented. Hence, the counter m now identifies a previously stored data point ($DP_m$) immediately following the previous data point ($DP_{m-1}$) at which the previous window was initialized. The previous median NIR signal value associated with the previous window is updated in a block 188 by taking the median of a NIR signal value ($NS_m$) stored at the previous data point $DP_m$ and two prior NIR signal values ($NS_{m-1}$ and $NS_{m-2}$) stored at previous data points ($DP_{m-1}$ and $DP_{m-2}$). The previous median pH level is updated in a block 190 by taking the median of the pH level ($pH_m$) at previous data point $DP_m$ and two prior pH levels ($pH_{m-1}$ and $pH_{m-2}$) stored at previous data points ($DP_{m-1}$ and $DP_{m-2}$).

Next, the current window must be updated. Accordingly, the counter n is incremented in a block 192. In a block 194, green reference value $GR_n$, NIR reference value $NR_n$, a green signal value $GS_n$ and a NIR signal value $NS_n$ recorded at data point $DP_n$ are stored. In a block 196, wavelength ratio $\lambda_n$ and pH level $pH_n$ are calculated as previously described. Finally, the logic returns to blocks 180 and 182, where the values comprising the current window are updated. The current median NIR signal value associated with the current window is updated in block 180 by taking the median of NIR signal value $NS_n$ at data point $DP_n$ and two prior NIR, signal values $NS_{n-1}$ and $NS_{n-2}$ at data points $DP_{n-1}$ and $DP_{n-2}$. The current median pH level is updated in block 182 by taking the median of the pH level $pH_n$ at data point $DP_n$ and two prior pH levels $pH_{n-1}$ and $pH_{n-2}$ at data points $DP_{n-1}$ and $DP_{n-2}$.

The values comprising the previous and current windows are continually updated as described above until a kink is finally detected in decision block 184. Hence, when there has been a significant change in NIR, signal values accompanied by a significant change in pH level, the logic proceeds to a block 198 in FIG. 6C, where the microcontroller 42 issues a kink warning by displaying a warning message on display 60. The warning message notifies the operator that a kink has occurred. In a preferred embodiment of the warning algorithm, the microcontroller 42 also discontinues or "dashes out" a message displaying the pH level monitored by the fiber-optic sensor 11. It will be appreciated that for any remaining parameters, such as the $CO_2$ parameter, the microcontroller will continue displaying the level of the parameter, unless the optical fiber being used to monitor that parameter is being affected by the kink as well. Hence, only those parameters' levels being affected by the kink are "dashed out" upon the display.

Although the result of decision block 184 may be positive and a kink warning is issued, it is possible that a permanent kink has not occurred, and that the significant change in NIR signal values and pH levels are merely the result of transient conditions. For example, movement by the patient may cause a slight kink in the optical fiber 17 that is sufficiently great to interfere with the green and NIR light signals being transmitted through the fiber-optic sensor. Consequently, the microcontroller 42 must wait for such transient conditions to disappear, e.g., by operator removal of the kink, and then determine if a permanent kink exists.

However, before waiting for the transients to disappear and comparing the current and previous windows, the microcontroller 42 stores the previous median NIR signal value as a pre-kink NIR signal value and the previous median pH level as a pre-kink pH level in a block 200. The previous data point counter m is reinitialized in a block 202 so that it equals the data point counter n and identifies the data point at which the kink was initially detected.

Once the previous data point counter m is initialized, the microcontroller waits for 120 seconds for any transient conditions to disappear. During this 120 second waiting period, the microcontroller continues to store and calculate green and NIR reference and signal values, wavelength ratios and the pH levels for twelve consecutive data points. More specifically, in a block 204, the data point counter n is incremented, while in a block 206 green reference value $GR_n$, NIR reference value $NR_n$, green signal value $GS_n$ and NIR signal value $NS_n$ recorded at consecutive data point $DP_n$ are stored. In a block 208, wavelength ratio $\lambda_n$ and pH level $pH_n$ are calculated as previously described. Finally, in decision block 210, the logic determines if the data point counter n is equal to the previous data point counter m plus 12. In other words, the logic determines if 120 seconds have passed since the pre-kink NIR and pH values have been determined. If the results are negative the logic returns to block 204 and repeats blocks 204 through 208 until the 120 second waiting period has expired. When the results of decision block 210 are positive, the logic proceeds to blocks 212 and 214 where the values comprising the current window are updated.

Figure 6A:
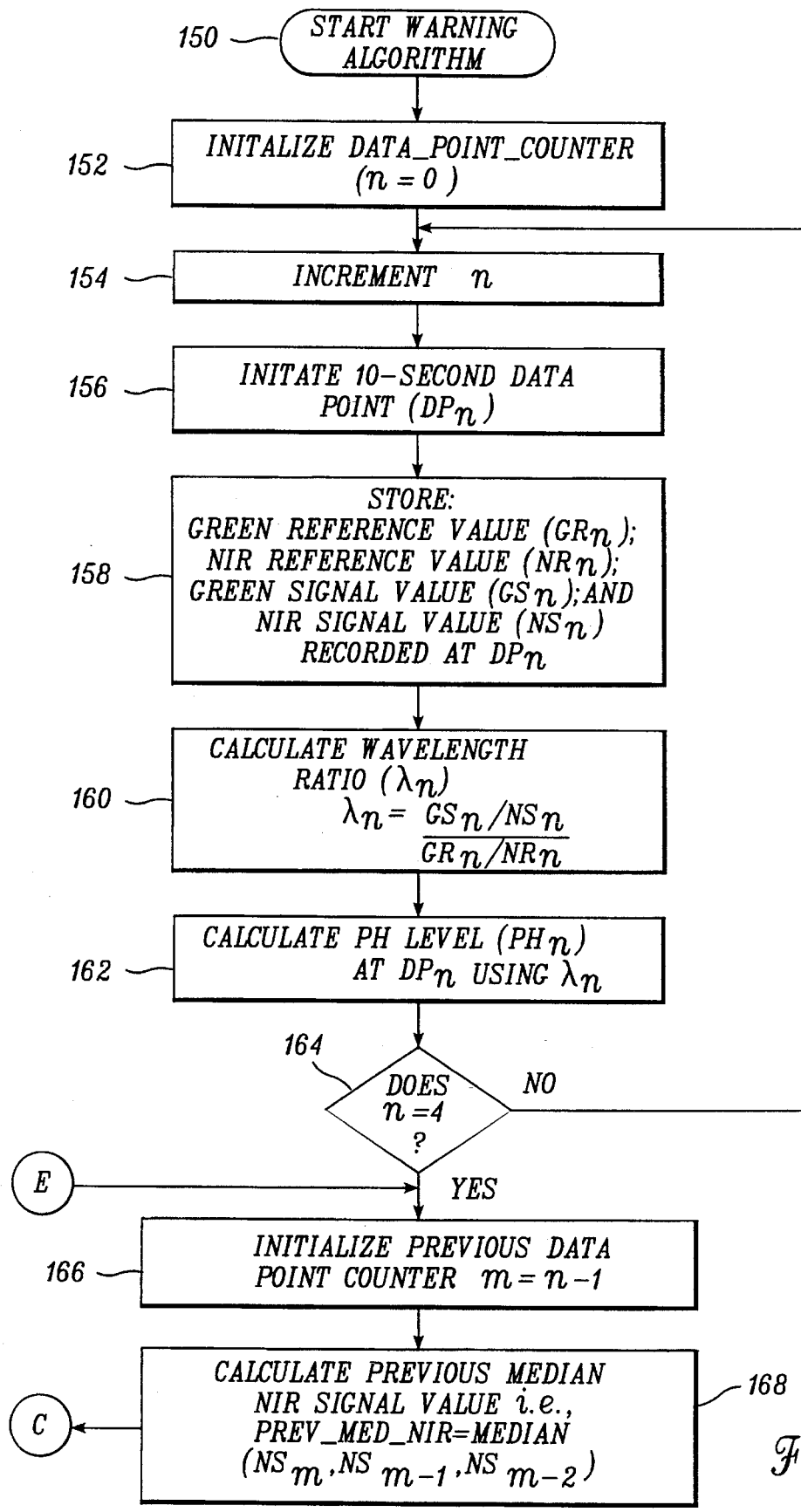
FIGS. 6A, 6B, 6C and 6D are flow charts illustrating the steps used to detect a kink in the optical fiber and issue a warning.
Figure 6B:
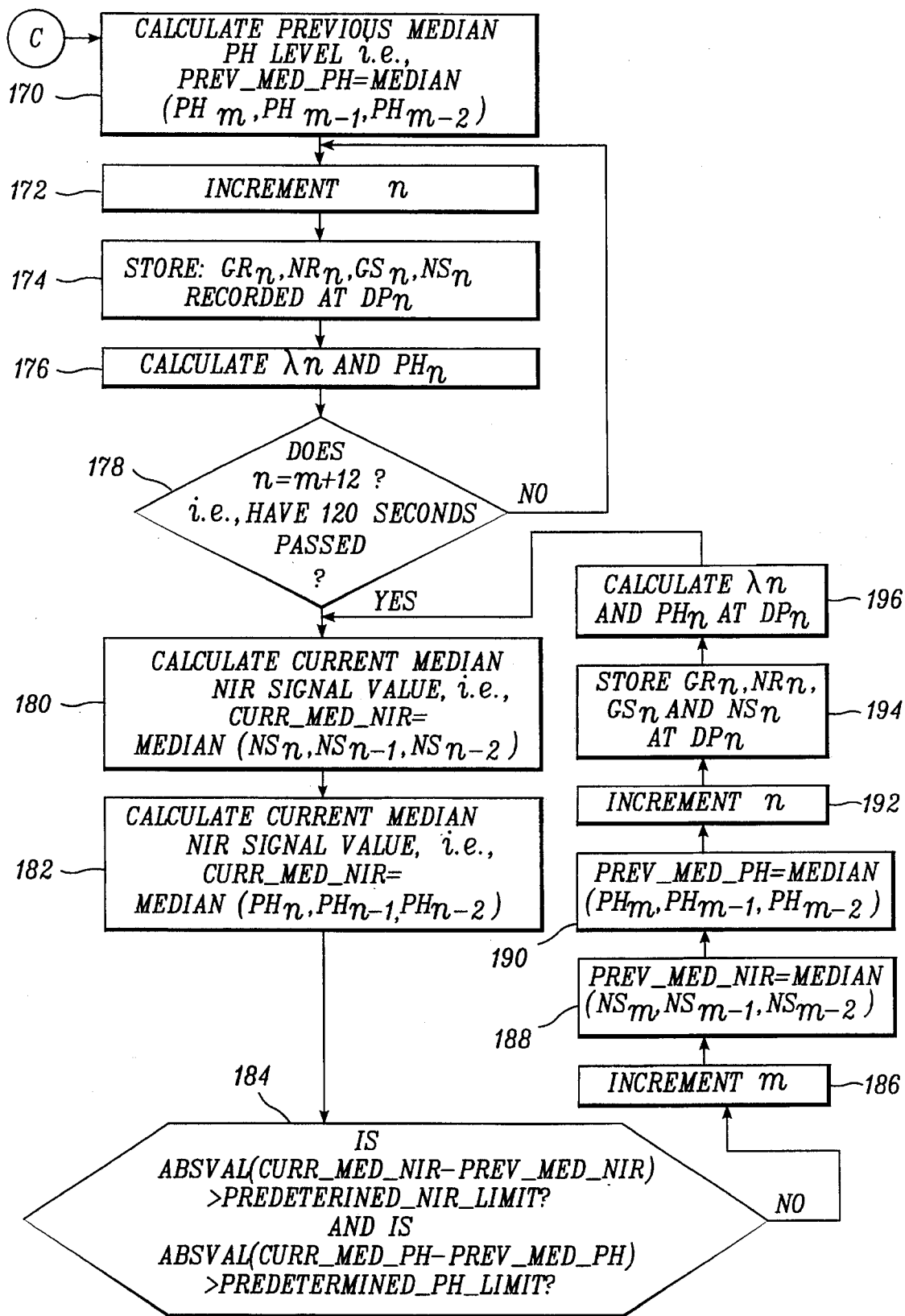
Figure 6C:
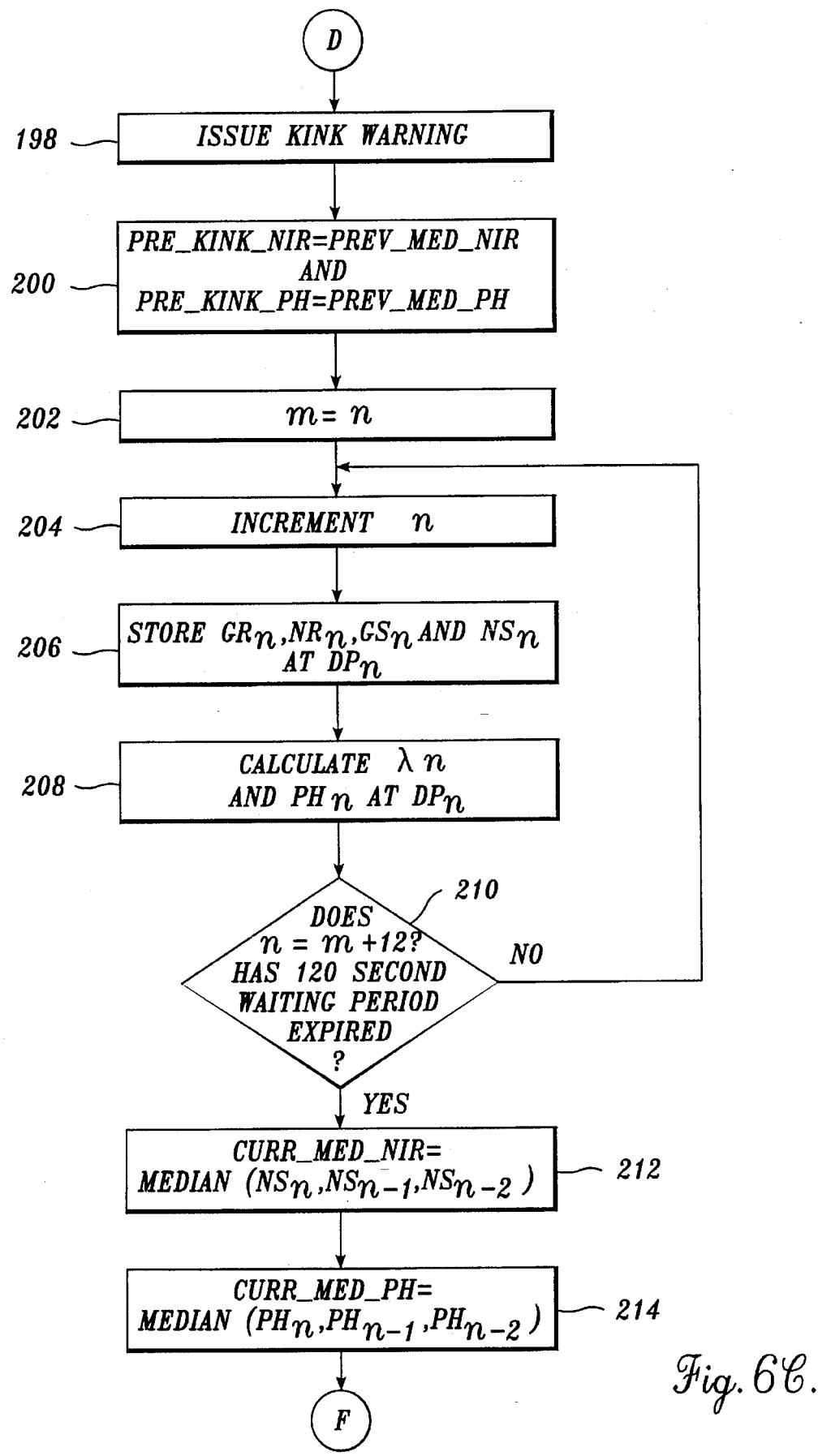
Figure 6D:
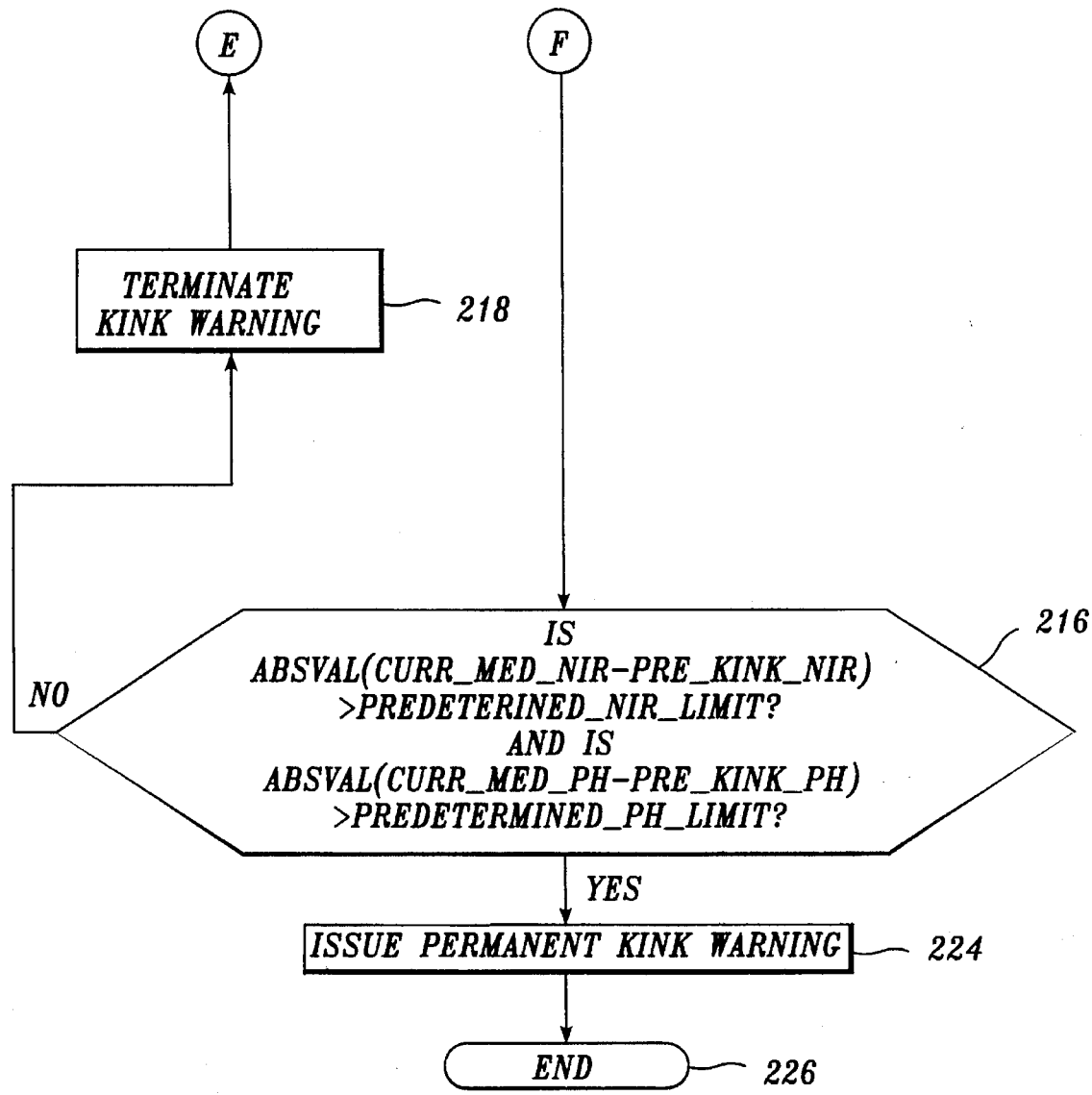

Once the values comprising the current window has been updated, the logic proceeds to a block 216 in FIG. 6D, where it compares the values of the current window and the pre-kink NIR and pH values in order to confirm that a permanent kink exists. In other words, the logic determines if the absolute value of a difference between the current median NIR signal value and the pre-kink NIR signal value is greater than the predetermined NIR signal value limit; and if an absolute value of a difference between the current median pH level and the pre-kink median pH level is greater than the predetermined pH level limit. If the result is positive, the logic proceeds to blocks 224 and 226 where a permanent kink warning is activated by the microcontroller and the warning algorithm ends. Consequently, the kink warning remains associated with the fiber-optic sensor 11 for the rest of its life. In the preferred embodiment of the present invention, the pH level displayed upon display 60 is permanently dashed out since the parameter is no longer being monitored. It should be recognized that parameters, such as the $CO_2$ parameter, whose optical fibers remain unaffected by the kink will continue to appear on display 60 and that the warning algorithm continues with respect to those parameters and optical fibers.

If the result of decision block 216 is negative, a permanent kink did not occur. Consequently, the logic proceeds to in a block 218, where the kink warning is terminated and the warning message disappears from the display 60. The microcontroller 42 then continues to store and calculate the green and NIR reference and signal values, wavelength ratio and pH level and continues to compare the previous and current windows until a kink is detected. However, one will note that the values comprising the previous window have not been updated since the possible kink was detected 120 seconds earlier. Hence, the previous window and the current window are 240 seconds apart at this point in the warning algorithm. The values comprising the previous window must be updated so that only 120 seconds separate the current and previous window.

Accordingly, the logic returns to block 166 in FIG. 6A, where the previous data point counter m is reinitialized so that it equals the data point counter n minus one, and identifies the data point $DP_m$ immediately preceding the most recently recorded data point $DP_n$. The previous window is then updated in blocks 168 and 170 using the previous data points $DP_m$, $DP_{m-1}$ and $DP_{m-1}$ stored immediately preceding the most recently recorded data point $DP_n$. The previous median NIR signal value associated with the previous window is updated in block 168 by taking the median of NIR signal values $NS_m$, $NS_{m-1}$ and $NS_{m-2}$ at data points $DP_m$, $DP_{m-1}$ and $DP_{m-2}$, while the previous median pH level is updated in block 170 by taking the median of the pH levels $pH_m$, $pH_{m-1}$ and $pH_{m-2}$ at data points $DP_m$, $DP_{m-1}$ and $DP_{m-2}$. The logic then repeats blocks 172 through 182 until the current window and the previous window are again 120 seconds apart. It should be recognized that updating the previous window as described above causes the previous window to skip the data points at which transient conditions affected the green and NIR signal values. Consequently, the data points at which transient conditions were present are not used to calculate the previous window, and thus, are not used to detect a kink.

Once the previous window and the current window have been updated so that they are 120 seconds apart, the logic proceeds to block 184, and again compares the current and previous windows to determine if a kink has occurred. Thus, blocks 184 through 216 (and, when necessary, blocks 166 through 182) are repeated and testing for a kink in optical fiber 17 continues for the remaining life of the fiber-optic sensor 11, or until a permanent kink occurs and a final warning is issued. While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for detecting and compensating for a kink in an optical fiber having a distal sensor for monitoring at least one parameter in an environment, wherein the optical fiber conveys light signals of a first wavelength and light signals of a second wavelength to and from the distal sensor, and wherein a photodetector records signal and reference values for the light signals of the first wavelength and for the light signals of the second wavelength at consecutive data points, the method comprising the steps of:

(a) at a current data point,
  (i) storing a current signal value and a current reference value for the light signal of the first wavelength;
  (ii) storing a current signal value and a current reference value for the light signal of the second wavelength; and
  (iii) calculating a current ratio as a function of the current signal value for the light signal of the first wavelength, the current signal value for the light signal of the second wavelength, the current reference value for the light signal of the first wavelength and the current reference value for the light signal of the second wavelength;

(b) at a next consecutive data point,
  (i) storing a next signal value and a next reference value for the light signal of the first wavelength;
  (ii) storing a next signal value and a next reference value for the light signal of the second wavelength; and
  (iii) calculating a next ratio as a function of the next signal value for the light signal of the first wavelength, the next signal value for the light signal of the second wavelength, the next reference value for the light signal of the first wavelength and the next reference value for the light signal of the second wavelength;

(c) repeating steps (a) and (b) until a kink is detected in the optical fiber by determining if a difference between the current signal value for the light signal of the second wavelength and the next signal value for the light signal of the second wavelength is greater than a predetermined limit;

(d) after the kink is detected in step (c) calculating a true measurement of the parameter that compensates for the kink at each data point affected by the kink.

2. The method of claim 1, the step of calculating the true measurement of the parameter at each data point further comprising the steps of:

after the kink is detected in step (c), (a) identifying the current data point as a pre-kink data point by:
  (i) storing the current signal value for the light signal of the first wavelength as a pre-kink signal value for the light signal of the first wavelength;
  (ii) storing the current signal value for the light signal of the second wavelength as a pre-kink signal value for the light signal of the second wavelength;
  (iii) storing the current reference value for the light signal of the first wavelength as a pre-kink reference value for the light signal of the first wavelength;
  (iv) storing the current reference value for the light signal of the second wavelength as a pre-kink signal value for the light signal of the second wavelength; and
  (v) storing the current ratio as a pre-kink ratio;

(b) identifying the next consecutive data point as a kink data point by:
  (i) storing the next signal value for the light signal of the first wavelength as a kink signal value for the light signal of the first wavelength;
  (ii) storing the next signal value for the light signal of the second wavelength as a kink signal value for the light signal of the second wavelength;
  (iii) storing the next reference value for the light signal of the first wavelength as a kink reference value for the light signal of the first wavelength;
  (iv) storing the next reference value for the light signal of the second wavelength as a kink reference value for the light signal of the second wavelength; and
  (v) storing the next ratio as a kink ratio.

3. The method of claim 2, the step of calculating the true measurement of the parameter further comprising the step of defining a linear relationship between the kink data point and the pre-kink data point, the step of defining the linear relationship comprising the steps of:

(a) calculating a slope of a line formed between the kink data point and the pre-kink data point; and (b) calculating an intercept of the line.

4. The method of claim 3, the step of calculating the true measurement of the parameter at each data point further comprising the steps of:

at the kink data point, (a) determining a true kink signal value for the light signal of the first wavelength that compensates for the kink based upon the linear relationship between the kink data point and the pre-kink data point;

(b) determining a true kink ratio as a function of the true kink signal value for the light signal of the first wavelength, the kink signal value for the light signal of the second wavelength, the kink reference value for the light signal of the first wavelength, and the kink reference value for the light signal of the second wavelength; and (c) determining the true measurement of the parameter as a function of the true kink ratio.

5. The method of claim 4, the step of determining the true kink signal value for the light signal of the first wavelength further comprising the steps of:

(a) calculating a first interim value for the light signal of the first wavelength as a function of the slope, intercept and kink signal value for the light signal of the second wavelength;

(b) determining an environmental effect on the kink signal value for the light signal of the first wavelength as a function of the kink signal value for the light signal of the first wavelength and the first interim value for the light signal of the first wavelength;

(c) determining a second interim value for the light signal of the first wavelength as a function of the kink signal value for the light signal of the second wavelength and a signal ratio of the pre-kink signal value for the light signal of the first wavelength to the pre-kink signal value for the light signal of the second wavelength; and (d) determining the true kink signal value for the light signal of the first wavelength as a function of the second interim value and the environmental effect.

6. The method of claim 4, the step of calculating the true measurement of the parameter further comprising the steps of:

at each subsequent data point affected by the kink, (a) storing a subsequent signal value and a subsequent reference value for the light signal of the first wavelength;

(b) storing a subsequent signal value and a subsequent reference value for the light signal of the second wavelength;

(c) determining a true subsequent signal value for the light signal of the first wavelength that compensates for the kink based upon the linear relationship between the kink data point and the pre-kink data point;

(b) determining a true subsequent ratio as a function of the true subsequent signal value for the light signal of the first wavelength, the subsequent signal value for the light signal of the second wavelength, the subsequent reference value for the light signal of the first wavelength, and the subsequent reference value for the light signal of the second wavelength; and (c) determining the true measurement of the parameter as a function of the true subsequent ratio.

7. The method of claim 6, the step of determining the true subsequent signal value for the light signal of the first wavelength further comprising the steps of:

(a) calculating a first interim value for the light signal of the first wavelength as a function of the slope, intercept and subsequent signal value for the light signal of the second wavelength;

(b) determining an environmental effect on the subsequent signal value for the light signal of the first wavelength as a function of the subsequent signal value for the light signal of the first wavelength and the first interim value for the light signal of the first wavelength;

(c) determining a second interim value for the light signal of the first wavelength as a function of the subsequent signal value for the light signal of the second wavelength and a signal ration of pre-kink signal value for the light signal of the first wavelength to pre-kink signal value for the light signal of the second wavelength; and (d) determining the true subsequent signal value for the light signal of the first wavelength as a function of the second interim value and the environmental effect.

8. The method of claim 1, the step of calculating the current ratio further comprising the steps of:

(a) determining a current signal ratio of the current signal value for the light signal of the first wavelength to the current signal value for the light signal of the second wavelength;

(b) determining a current reference ratio of the current reference value for the light signal of the first wavelength to the current reference value for the light signal of the second wavelength; and (c) dividing the current signal ratio by the current reference ratio.

9. The method of claim 8, the step of calculating the next ratio further comprising the steps of:

(a) determining a next signal ratio of the next signal value for the light signal of the first wavelength to the next signal value for the light signal of the second wavelength;

(b) determining a next reference ratio of the next reference value for the light signal of the first wavelength to the next reference value for the light signal of the second wavelength; and (c) dividing the next signal ratio by the next reference ratio.

10. The method of claim 1, wherein the light signal of the first wavelength is a light signal of a wavelength in the green region of the visible spectrum and the light signal of the second wavelength is a light signal of a wavelength in the near infrared region of the electromagnetic spectrum.

11. The method of claim 1, wherein the current and next data points are 10 seconds apart.

12. The method of claim 1, wherein the post-kink data points are 10 seconds apart.

13. The method of claim 1, wherein a plurality of optical fibers have a distal sensor for monitoring a plurality of parameters in the environment, wherein each optical fiber conveys light signals of a first wavelength and light signals of a second wavelength to and from the distal sensor, and wherein a photodetector for each optical fiber records the signal and reference values for the light signals of the first wavelength and the signal and reference values for the light signals of the second wavelength conveyed by that optical fiber at consecutive data points, the method comprising the step of simultaneously repeating steps (a) through (d) for each optical fiber.

14. The method of claim 13, wherein a first optical fiber is used to monitor a pH parameter in a blood gas environment, and a second optical fiber is used to monitor a carbon dioxide parameter in the blood gas environment, and steps (a) through (d) are simultaneously repeated for the first and the second optical fiber.

15. An apparatus for detecting and compensating for a kink in an optical fiber, wherein the optical fiber conveys light signals of a first wavelength and light signals of a second wavelength, the apparatus comprising:

(a) a distal sensor that monitors a level of a parameter in an environment in which the distal sensor is immersed, wherein the distal sensor is disposed at a tip of the optical fiber and the optical fiber conveys light signals of the first wavelength and light signals of the second wavelength to and from the distal sensor;

(b) a photodetector that records reference values for the light signals of the first wavelength and for the light signals of the second wavelength conveyed to the distal sensor by the optical fiber at consecutive data points, and wherein the photodetector records signal values for the light signals of the first wavelength and for light signals of the second wavelength conveyed from the distal sensor at consecutive data points;

(c) a processing unit electronically coupled to the photodetector to receive the signal and reference values for the light signals of the first wavelength and the signal and reference values for the light signals of the second wavelength, said processing unit including memory means for storing program instructions, which control the processing unit so that it comprises:

(i) storing means for storing the signal and reference values for the light signals of the first wavelength and the signal and reference values for the light signals of the second wavelength recorded by the photodetector at consecutive data points;

(ii) detecting means for detecting the kink in the optical fiber, wherein an effect of the kink is to change the signal values for the light signals of the first wavelength and the signal values for the light signals of the second wavelength, wherein the detecting means determines if a change between the signal values for light signals of the second wavelength recorded at a pair consecutive data points is greater than a predetermined threshold; and (iii) measuring means for measuring an accurate level of the parameter in the environment after the kink is detected, wherein the measuring means compensates for the effect of the kink.

16. The apparatus of claim 15, wherein the measuring means compensates for the effect of the kink at consecutive data points after the kink is detected by:
 (a) determining an accurate signal value for light signals of the first wavelength; and
 (b) measuring the accurate level of the parameter in the environment as a function of the accurate signal value for the light signals of the first wavelength, the signal value for the light signals of the second wavelength, the reference value for the lights signals of the first wavelength, and the reference value for the light signals of the second wavelength.

17. The apparatus of claim 16, wherein the measuring means determines the accurate signal value for the light signals of the first wavelength by:
 (a) determining a first temporary signal value for the light signals of the first wavelength that linearly corresponds to the change between the signal values for the light signals of the second wavelength recorded at the pair of consecutive data points;
 (b) determining an effect of a change in the environment on the signal values of the first wavelength by offsetting the first temporary signal value for the light signals of the first wavelength;
 (c) determining a second temporary signal value for the light signals of the first wavelength that factors out the effect of the kink on the signal values of the first wavelength; and
 (d) combining the second temporary signal value and the effect of the change in the environment.

18. The apparatus of claim 17, wherein the light signal of the first wavelength is a light signal of a wavelength in the green region of the visible spectrum and the light signal of the second wavelength is a light signal of a wavelength in the near infrared region of the electromagnetic spectrum.

19. The apparatus of claim 18, wherein the distal sensor monitors levels of a plurality of parameters in the environment, wherein the distal sensor is disposed at tips of a plurality of optical fibers and each optical fiber conveys light signals of the first wavelength and light signals of the second wavelength to and from the distal sensor.

20. The apparatus of claim 19, further comprising a plurality of photodetectors, wherein each photodetector records the signal and reference values for the light signals of the first wavelength and the signal and reference values for the light signals of the second wavelength conveyed by each of the optical fibers at consecutive data points.

21. The apparatus of claim 20, wherein the processing unit is electronically coupled to each of the photodetectors and detects and compensates for kink in each of the optical fibers.

22. The apparatus of claim 21, wherein a first optical fiber is used to monitor a pH parameter in a blood gas environment, and a second optical fiber is used to monitor a carbon dioxide parameter in the blood gas environment.

23. A method for issuing a warning after detecting a kink in an optical fiber having a distal sensor for monitoring a level of a parameter in an environment, wherein the optical fiber conveys light signals of a first wavelength and light signals of a second wavelength to and from the distal sensor, wherein a photodetector records reference values for the light signals of the first wavelength and for the light signals of the second wavelength conveyed to the distal sensor at consecutive data points, and wherein the photodetector records signal values for the light signals of the first wavelength and for the light signals of the second wavelength conveyed from the distal sensor at consecutive data points, the method comprising the steps of:
 (a) updating a current window of data, the data comprising a current median signal value for the light signal of the second wavelength and a current median level of the parameter;
 (b) updating a previous window of data, the data comprising a previous median signal value for the light signal of the second wavelength and a previous median level of the parameter;
 (c) comparing the current window of data to the previous window of data until the kink is detected in the optical fiber by:
  (i) determining if a difference between the current median signal value for the light signal of the second wavelength and the previous median signal value of the light signal of the second wavelength is greater than a predefined signal value threshold; and
  (ii) determining if a difference between the current median level and the previous median level is greater than a predefined parameter threshold; and
 (d) issuing a warning that the kink has occurred after determining that the predefined parameter threshold has been exceeded step (c).

24. The method of claim 23, the step of updating the current window of data further comprising the steps of:
 (a) determining the current median signal value for the light signal of the second wavelength as a function of three most recently recorded signal values for the light signal of the second wavelength; and
 (b) determining the current median level of the parameter as a function of three most recently calculated current levels of the parameter.

25. The method of claim 24, wherein a current level of the parameter is calculated by:
 (a) determining a current signal value ratio of the signal value for the light signal of the first wavelength to the signal value for the light signal of the second wavelength;
 (b) determining a current reference value ratio of the reference value for the light signal of the first wavelength to the reference value for the light signal of the second wavelength;
 c) determining a current wavelength ratio by dividing the current signal value ratio by the current reference value ratio; and
 (d) calculating a current level of the parameter as a function of the current wavelength ratio.

26. The method of claim 25, the step of updating the previous window of data further comprising the steps of:
 (a) determining the previous median signal value for the light signal of the second wavelength as a function of three previously recorded signal values for the light signal of the second wavelength; and
 (b) determining the previous median level of the parameter as a function of three previously calculated previous levels of the parameter.

27. The method of claim 26, wherein a previous level of the parameter is calculated by:
 (a) determining a previous signal value ratio of a previously recorded signal value for the light signal of the first wavelength to a previously recorded signal value for the light signal of the second wavelength;
 (b) determining a previous reference value ratio of a previously recorded reference value for the light signal of the first wavelength to a previously recorded reference value for light signal of the second wavelength;

(c) determining a previous wavelength ratio by dividing the previously recorded signal value ratio by the previously recorded reference value ratio; and (d) calculating a previous level of the parameter as a function of the previous wavelength ratio.

28. The method of claim 27, wherein the three previously recorded signal values for the light signals of the first wavelength and three previously recorded signal values for the light signals of the second wavelength were recorded at least 120 seconds earlier than the three most recently recorded signal values for the light signals of the first wavelength and three most recently recorded signal values of the second wavelength.

29. The method of claim 23, further comprising the steps of, (a) temporarily suspending updating the previous window of data during a predefined time interval;

(b) after suspending the previous window, storing the previous window of data as a pre-kink window of data by:

(i) storing the previous signal value for the light signal of the second wavelength as a pre-kink signal value for the light signal of the second wavelength; and (ii) storing the previous level as a pre-kink level;

(c) continuing updating the current window of data during the predefined time interval;

(d) after the predefined time interval, comparing the current window of data to the pre-kink window of data in order to detect a permanent kink by:

(i) determining if a difference between the current signal value for the light signal of the second wavelength and the pre-kink signal value of the light signal of the second wavelength is greater than a predefined signal value threshold; and (ii) determining if a difference between the current level and the pre-kink level is greater than a predefined parameter threshold; and (e) after detecting the permanent kink in step (d), issuing a final warning that the permanent kink has occurred; and (f) after issuing the final warning in step (e), permanently suspending the monitoring of the level of the parameter.

30. The method of claim 23, wherein the light signal of the first wavelength is a light signal of a wavelength in the green region of the visible spectrum and the light signal of the second wavelength is a light signal of a wavelength in the near infrared region of the electromagnetic spectrum.

31. The method of claim 23, wherein a plurality of optical fibers have a distal sensor for monitoring a plurality of parameters in the environment, wherein each optical fiber conveys light signals of a first wavelength and light signals of a second wavelength to and from the distal sensor, and wherein a photodetector for each optical fiber records the light signals of the first wavelength and the light signals of the second wavelength conveyed by that optical fiber at consecutive data points, the method further comprising the step of simultaneously repeating steps (a) through (d) for each optical fiber.

32. A method for detecting and compensating for a kink in an optical fiber having a distal sensor for monitoring at least one parameter in an environment, wherein the optical fiber conveys light signals of a first wavelength and light signals of a second wavelength to and from the distal sensor, and wherein a photodetector records signal and reference values for the light signals of the first wavelength and for the light signals of the second wavelength at consecutive data points, the method comprising the steps of:

(a) at a current data point, (i) storing a current signal value and a current reference value for the light signal of the first wavelength;

(ii) storing a current signal value and a current reference value for the light signal of the second wavelength; and (iii) calculating a current ratio as a function of the current signal value for the light signal of the first wavelength, the current signal value for the light signal of the second wavelength, the current reference value for the light signal of the first wavelength and the current reference value for the light signal of the second wavelength;

(b) at a next consecutive data point, (i) storing a next signal value and a next reference value for the light signal of the first wavelength;

(ii) storing a next signal value and a next reference value for the light signal of the second wavelength; and (iii) calculating a next ratio as a function of the next signal value for the light signal of the first wavelength, the next signal value for the light signal of the second wavelength, the next reference value for the light signal of the first wavelength and the next reference value for the light signal of the second wavelength;

(c) repeating steps (a) and (b) until a kink is detected in the optical fiber by determining if a difference between the current signal value for the light signal of the second wavelength and the next signal value for the light signal of the second wavelength is greater than a predetermined limit; and (d) calculating a true level of the parameter that compensates for the kink at each data point based on a linear relationship existing between the current signal values for the light signal of the first wavelength and the light signals of the second wavelength, and the next signal values for the light signals of the first wavelength and the light signals of the second wavelength when the kink is detected in step (c).

33. The method of claim 32, the step of calculating the true level of the parameter further comprising the step of defining the linear relationship existing between the current signal values and the next signal values when the kink is detected in step (c), the step of defining the linear relationship further comprising the steps of:

(a) calculating a slope of a line formed between a kink data point defined by the next signal value for the light signal of the first wavelength and the next signal value for the light signal of the second wavelength, and a pre-kink data point defined by the current signal value for the light signal of the first wavelength and the current signal value for the light signal of the second wavelength; and (b) calculating an intercept of the line.

34. The method of claim 33, the step of calculating the true level of the parameter further comprising the steps of:

when the kink is detected in step (c), (a) determining a true signal value for the light signal of the first wavelength for the next data point that compensates for the kink based upon the linear relationship between the kink data point and the pre-kink data point;

(d) determining a true ratio for the next data point as a function of the true signal value for the light signal of the first wavelength, the next reference value for the light signal of the first wavelength, the next signal value for the light signal of the second wavelength, and the next reference value for the light signal of the second wavelength; and (e) determining the true level of the parameter for the next data point as a function of the true ratio.

35. The method of claim 34, the step of determining the true signal value for the light signal of the first wavelength further comprising the steps of:

(a) calculating a first interim value for the light signal of the first wavelength as a function of the slope, intercept and next signal value for the light signal of the second wavelength;

(b) determining an environmental effect on the next signal value for the light signal of the first wavelength as a function of the next signal value for the light signal of the first wavelength and the first interim value for the light signal of the first wavelength;

(c) determining a second interim value for the light signal of the first wavelength as a function of the next signal value for the light signal of the second wavelength and the current ratio; and (d) determining the true signal value for the light signal of the first wavelength as a function of the second interim value and the environmental effect.

36. The method of claim 34, the step of calculating the true level of the parameter further comprising the steps of:

at each data point after the kink is detected, (a) storing a kinked signal value and a kinked reference value for the light signal of the first wavelength;

(b) storing a kinked signal value and a kinked reference value for the light signal of the second wavelength;

(c) determining the true signal value for the light signal of the first wavelength that compensates for the kink based upon the linear relationship between the kink data point and the pre-kink data point;

(d) determining the true ratio as a function of the true signal value for the light signal of the first wavelength, the kinked reference value for the light signal of the first wavelength, the kinked signal value for the light signal of the second wavelength and the kinked reference value for the light signal of the second wavelength; and (e) determining the true level of the parameter as a function of the true ratio.

37. The method of claim 36, the step of determining the true signal value for the light signal of the first wavelength further comprising the steps of:

(a) calculating the first interim value for the light signal of the first wavelength as a function of the slope, intercept and kinked signal value for the light signal of the second wavelength;

(b) determining an environmental effect on the kinked signal value for the light signal of the first wavelength as a function of the kinked signal value for the light signal of the first wavelength and the first interim value for the light signal of the first wavelength;

(c) determining a second interim value for the light signal of the first wavelength as a function of the kinked signal value for the light signal of the second wavelength and the current ratio; and (d) determining the true signal value for the light signal of the first wavelength as a function of the second interim value and the environmental effect.

38. The method of claim 32, wherein the light signal of the first wavelength is a light signal of a wavelength in the green region of the visible spectrum and the light signal of the second wavelength is a light signal of a wavelength in the near infrared region of the electromagnetic spectrum.

39. The method of claim 32, wherein the current and next data points are 10 seconds apart.

40. The method of claim 36, wherein the data points after the kink is detected are 10 seconds apart.

41. The method of claim 32, wherein a plurality of optical fibers have a distal sensor for monitoring a plurality of parameters in the environment, wherein each optical fiber conveys light signals of a first wavelength and light signals of a second wavelength to and from the distal sensor, and wherein a photodetector for each optical fiber records the signal and reference values for the light signals of the first wavelength and the signal and reference values for the light signals of the second wavelength conveyed by that optical fiber at consecutive data points, the method comprising the step of simultaneously repeating steps (a) through (d) for each optical fiber.

42. The method of claim 41, wherein a first optical fiber is used to monitor a pH parameter in a blood gas environment, and a second optical fiber is used to monitor a carbon dioxide parameter in the blood gas environment, and steps (a) through (d) are repeatedly simultaneously for the first and the second optical fiber.

* * * * *

UNITED STATES PATENT AND TRADEMARK OFFICE
CERTIFICATE OF CORRECTION

PATENT NO. : 5,565,976   Page 1 of 2
DATED : October 15, 1996
INVENTOR(S) : B. Fieggen et al.

It is certified that error appears in the above-indentified patent and that said Letters Patent is hereby corrected as shown below:

| COLUMN | LINE | |
|---|---|---|
| 17 (Claim 7, | 33 line 16) | "a signal ration" should read --a signal ratio-- |
| 18 (Claim 15, | 62 line 38) | "pair consecutive" should read --pair of consecutive-- |
| 19 (Claim 16, | 10 line 10) | "the lights signals" should read --the light signals-- |
| 19 (Claim 21, | 51 line 3) | "for kink" should read --for the kink-- |
| 20 (Claim 23, | 24 line 35) | "exceeded step" should read --exceeded in step-- |
| 20 (Claim 25, | 45 line 11) | "c) determining a current" should read --(c) determining a current-- |
| 21 (Claim 27, | 2 line 10) | "for light" should read --for the light-- |

UNITED STATES PATENT AND TRADEMARK OFFICE
CERTIFICATE OF CORRECTION

PATENT NO. : 5,565,976
DATED : October 15, 1996
INVENTOR(S) : B. Fieggen et al.

Page 2 of 2

It is certified that error appears in the above-indentified patent and that said Letters Patent is hereby corrected as shown below:

| COLUMN | LINE | |
|---|---|---|
| 21 (Claim 29 | 17 lines 1-2) | "comprising the steps of," should read --comprising the steps of:-- |
| 24 (Claim 42 | 47 line 5) | "repeatedly" should read --repeated-- |

Signed and Sealed this

Twenty-fifth Day of February, 1997

Attest:

BRUCE LEHMAN

Attesting Officer

Commissioner of Patents and Trademarks